United States Patent [19]

Ehlis et al.

[11] Patent Number: 5,437,818
[45] Date of Patent: Aug. 1, 1995

[54] HYDRATES OF THE DISODIUM SALT OR DIPOTASSIUM SALT OF 4,4′-BIS(2-SULFOSTYRYL)BIPHENYL

[75] Inventors: Thomas Ehlis, Freiburg, Germany; André Geoffroy, Habsheim, France; Erwin Marti, Basel, Switzerland; Josef Zelger, Riehen, Switzerland; Karlheinz Franke, Basel, Switzerland; Andreas Burkhard, Basel, Switzerland

[73] Assignee: Ciba-Geigy Corporation, Ardsley, N.Y.

[21] Appl. No.: 81,597

[22] Filed: Jun. 23, 1993

[30] Foreign Application Priority Data

Jun. 30, 1992 [CH] Switzerland .................. 2042/92

[51] Int. Cl.⁶ .................. C09K 11/06; C07C 309/01
[52] U.S. Cl. .................. 252/301.21; 562/87
[58] Field of Search .................. 562/87; 252/301.21

[56] References Cited

U.S. PATENT DOCUMENTS 3,984,399 10/1976 Woeber et al. .................. 562/87
5,076,968 12/1991 Fringeli .................. 252/543

FOREIGN PATENT DOCUMENTS 0395374 9/1990 European Pat. Off. .
1583595 11/1969 France .
594617 1/1978 Switzerland .

*Primary Examiner*—José G. Dees
*Assistant Examiner*—Joseph M. Conrad, III
*Attorney, Agent, or Firm*—Kevin T. Mansfield

[57] ABSTRACT

The present invention relates to novel hydrates of the disodium salt or dipotassium salt of 4,4′-bis(2-sulfostyryl)biphenyl characterized by their water of hydration content, to the crystal forms associated therewith, characterized by their X-ray diffraction pattern, to processes for the preparation, and to their use for the preparation of concentrated formulations of fluorescent whitening agents.

38 Claims, No Drawings

HYDRATES OF THE DISODIUM SALT OR DIPOTASSIUM SALT OF 4,4′-BIS(2-SULFOSTYRYL)BIPHENYL

The present invention relates to novel hydrates of the disodium salt or dipotassium salt of 4,4′-bis(2-sulfostyryl)biphenyl characterised by their water of hydration content, to the crystal forms associated therewith, characterised by their X-ray diffraction pattern, to processes for the preparation, and to their use for the preparation of concentrated formulations of fluorescent whitening agents.

Fluorescent whitening agents are most recently preferably put on the market in the form of aqueous solutions or suspensions. To this end, for example, the moist filtercakes or else the dry powders are suspended in water. Dispersants and thickeners are added to the suspension in order to increase homogeneity, wettability and shelf life. Frequently an electrolyte is also added to these auxiliaries. Despite these additives, there are limits for the concentration of fluorescent whitening agent above which the suspensions often are no longer stable on storage and have poor metering characteristics. These limits can often not be reproduced since they depend on the particular pretreatment.

The reason for the different properties of a disodium salt of 4,4′-bis(2-sulfostyryl)biphenyl is the occurrence of anhydrates and hydrates having different crystal forms, such as are obtained in the preparation according to DE-A-17 93 482 and the subsequent purification with base and oxidising agent at high temperatures. Examples of the number of bound water molecules are compounds of the formula (I),

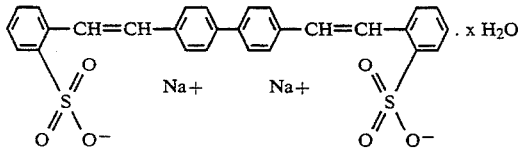

in which x is a number from 0 to 20, in particular 1, 2, 3, 5, 6, 7, 8, 9, 10, 11, 12, 13, 14 or 15.

Hereinafter, the term active substance refers to the compound of the formula (I) in which x is the number 0.

Surprisingly, it has now been found that formulations of fluorescent v, whitening agents having an active substance concentration of more than 30% by weight which are stable on storage and whose viscosity can be selectively set at a value within a wide range, can be prepared if a specific hydrate or mixtures of hydrates of the fluorescent whitening agents used, having a specific crystal form, or several specific crystal forms, are present.

Accordingly, the invention relates to novel hydrates of the disodium salt or dipotassium salt of 4,4′-bis(2-sulfostyryl)biphenyl whose crystal forms are characterised by X-ray diffraction diagrams which are essentially as in Table 1, 2, 3, 5 or 6.

The invention furthermore relates to a mixture of hydrates of the disodium salt of 4,4′-bis(2-sulfostyryl)biphenyl which is characterised by an X-ray diffraction diagram which is essentially as in Table 4.

The hydrates involved have:

a platelet-like crystal form which is designated as p form and characterised by an X-ray diffraction diagram which is essentially as in Table 1, a rod-like crystal form which is designated as i form and characterised by an X-ray diffraction diagram which is essentially as in Table 2, a rod-like crystal form which is designated as j form and characterised by an X-ray diffraction diagram which is essentially as in Table 3, a mixture of crystal forms i and j characterised by an X-ray diffraction diagram which is essentially obtained by additive superposition of the lines according to Tables 2 and 3 as shown in Table 4, a crystal form designated c form and characterised by an X-ray diffraction diagram which is essentially as in Table 5, and a crystal form of a novel hydrate of the dipotassium salt of 4,4′-bis(2-sulfostyryl)biphenyl which is characterised by an X-ray diffraction diagram which is essentially as in Table 6.

The platelet-like crystal form (p) consists for the most part of one or more hydrates of the formula (II)

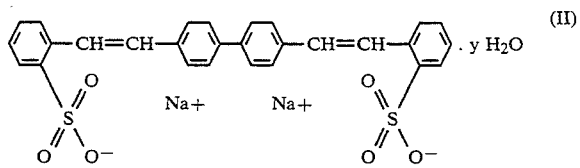

in which y is a number between 9 and 13.

The rod-like crystal forms (i or j) consist for the most part of one or more hydrates of the formula (III)

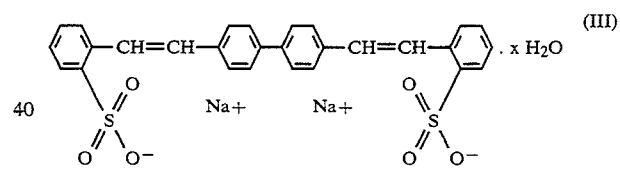

in which z is a number between 7 and 12.

The crystal form (c) consists for the most part of a hydrate of the formula (IV)

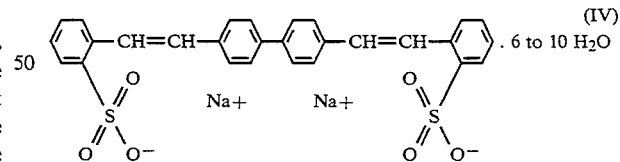

The crystal form of the novel hydrate of the dipotassium salt of 4,4′-bis(2-sulfostyryl)biphenyl consists for the most part of the hydrate of the formula (V)

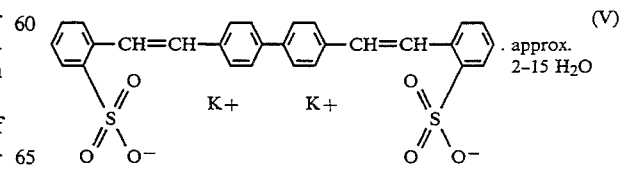

The amount of water of hydration is usually determined via differential thermal analysis or dynamic differential calorimeter in which the proportion of the unbound water, that is the water melting at 0° C., is measured, or by subsequent water analysis by methods such as Karl Fischer titration, thermogravimetric analysis or loss on drying at elevated temperature.

The platelet-like (p) hydrate can be prepared from an aqueous suspension of the hydrates in the rod-like form (i, j) or of a mixture of both salt-free hydrates at a maximum active substance content of 20% by weight by stirring for several hours at 5°–45° C. at a low shearing force. To obtain active substance concentrations of more than 30% by weight, the suspension thus formed can be concentrated via any customary methods, such as centrifugation, evaporation in vacuo, reverse osmosis or microfiltration.

A further possible preparation method is to inoculate an aqueous suspension of any desired hydrate of the disodium salt of 4,4'-bis(2-sulfostyryl)biphenyl with platelet-like (p) seed crystals. This variant has the advantage that any crystal form of the starting material and active substance concentrations of more than 30% by weight, preferably 30 to 50% by weight, can be used and thus the suspension obtained is formed in the desired concentration and does not have to be concentrated.

To this end, the disodium salt of 4,4'-bis(2-sulfostyryl)biphenyl obtained after synthesis and subsequent purification is advantageously suspended in water, the suspension is homogenised, the seed crystals are added, and the mixture is stirred. This stirring can be carried out continuously or intermittently, for example every 2 hours for 15 minutes. The duration of the reaction itself depends on the amount of seed crystals used and on the stirring rate and can be between 2 and 60 hours.

The seed crystal content is in general between 0.1 and 60% by weight, preferably between 1 and 50% by weight, and particularly preferably between 1 and 30% by weight, relative to the total active substance content. In all cases in which only a portion of the final compound is replaced by new starting material, the conversion can be carded out as semi-continuous or continuous process.

The reaction temperature for preparing the platelet-like (p) hydrate is in general 5°–45° C. and preferably 15°–40° C.

In a preferred measure, the rod-like form is converted into the platelet-form by inoculating an aqueous suspension of the rod-like form with the platelet. The seed crystals should be used in the form of small crystals whose average size does not exceed 10 micron. This allows the substantial reduction of the seed crystal content, for example down to 0.1 to 5% by weight, relative to the total active substance content. The conversion is preferably effected without stirring.

Another possibility for preparing the platelet-like form (p) is to add seed crystals to the dry material and leave the mixture in a thin layer at 20°–55° C. and a relative humidity of 90–100% for several days.

The hydrate which has the rod-like crystal form i in accordance with Table 2 is prepared by treating a concentrated aqueous suspension of any desired hydrate of the disodium salt of 4,4'-bis(2-sulfostyryl)biphenyl at a temperature of 70°–130° C. in a closed vessel or in a reflux apparatus for 2–12 hours, followed by cooling to room temperature. The active substance concentration of the suspension is preferably in the range from 30–60% by weight.

In a preferred embodiment, the production of the hydrate which has the rod-like crystal form j in accordance with Table 2 is effected by treating an aqueous suspension, containing 40 wt. % of any desired hydrate of the disodium salt of 4,4'-bis(2-sulfostyryl)biphenyl for 4 hours at a temperature of 95° C. in a closed vessel, and then cooling to room temperature.

The hydrate which has the rod-like crystal form j in accordance with Table 3 is prepared by treating a concentrated aqueous suspension of any desired hydrate of the disodium salt of 4,4'-bis(2-sulfostyryl)biphenyl at a temperature of 42°–70° C. in a closed vessel or in a reflux apparatus for 2 hours to 4 days, followed by cooling to room temperature. The active substance concentration of the suspension is preferably in the range from 30–60% by weight.

In a preferred embodiment, the production of the hydrate which has the rod-like crystal form j in accordance with Table 3 is effected by treating an aqueous suspension, containing 40 wt. % of disodium salt of 4,4'-bis(2-sulfostyryl)biphenyl in the platelet form for 4 hours at a temperature of 95° C. in a closed vessel, and then cooling to room temperature.

At temperatures of about 70° C., mixtures of the two rod-like crystal forms i and j can be obtained, at 70°–100° C. mostly i- and 50°–70° C. the j-form are obtained.

In all cases, the reaction time can be accelerated by addition of seed crystals.

The c hydrate can be prepared from an aqueous suspension of the hydrate in the i rod-like form of j rod-like form or in the p platelet-like form. The procedure is as follows: a portion of the water of the suspension is removed by a suitable method, for example centrifuging, followed by storage at a relative humidity set at 52% to up to 100% for a period ranging from hours to days. Suspensions prepared using this c hydrate and stabilised by addition of electrolyte are stable on storage at 50° C.

Suspensions of the hydrates i, j or p can also be converted directly into the c form by addition of at least about 5 wt. % NaCl, based on the total weight of the slurry, and stirring at room temperature or up to 100° C., and then cooling.

A suitable thermal analysis showed that the c hydrate is a 6 to 10 hydrate. It is also unambiguously characterised by determining the X-ray diffraction pattern.

The invention also provides aqueous formulations containing 30–50% by weight of active substance in the form of the disodium salt of 4,4'-bis(2-sulfostyryl)biphenyl in the platelet-like crystal form p. These formulations remain flowable, have good metering characteristics and are stable for months even after standing at temperatures of between 5°–40° C. for an extended period of time, they do not form sediments. In the order to achieve the lowest possible viscosity, the particle size of the maturity of platelets should advantageously be above 10 μm and macroscopic inclusion of air should be minimised.

The suspended product can be freed from fairly large agglomerates by homogenising it again and deaerating it under reduced pressure.

Aqueous formulations containing 30–50% by weight of active substance in the form of the disodium salt of 4,4'-bis(2-sulfostyryl)biphenyl in the rod-like crystal forms i and j are highly viscous when no formulation auxiliaries are added and are suitable for the production of brushable pastes or for being incorporated therein.

Thus, by mixing the hydrate having different crystal forms, a desired viscosity can be selectively established without any further auxiliaries. An electrolyte, for example NaCl or $Na_2SO_4$, can be admixed to these mixtures for stabilising the hydrates contained therein.

A particular advantage of these hydrates having different crystal forms is to enable ready-to-use and stable formulations of a wide range of viscosities to be produced without addition of ecologically harmful formulation auxiliaries.

However, the formulations thus obtained can also contain customary formulation auxiliaries, such as dispersions, builders, protective colloids, stabilisers, preservatives, perfuming agents and sequestering agents.

Dispersing agents are preferably anionic ones, such as condensation products of aromatic sulfonic acids with formaldehyde, such as ditolylethersulfonic acid, naphthalenesulfonates or ligninsulfonates.

Examples of suitable builders or protective colloids are modified polysaccharides derived from cellulose or heteropolysaccharides, such as xanthan, carboxymethylcellulose and polyvinyl alcohols (PVA), polyvinylpyrrolidones (PVP), polyethylene glycols (PEG) and aluminium silicates or magnesium silicates. They are usually used in a concentration range of 0.01 to 2% by weight and preferably 0.05 to 0.5% by weight, relative to the total weight of the formulation.

Examples of auxiliaries which can be used for stabilisation are ethylene glycol, propylene glycol or dispersants in an amount of 0.2 to 5% by weight and preferably 0.3 to 2% by eight, relative to the total weight of the formulation.

Compounds which are used as preservatives are 1,2-benzisothiazolin-3-one, formaldehyde or chloroacetamide in an amount of 0.1 to 1% by weight and preferably 0.1 to 0.5% by weight relative to the total weight of the formulation.

The concentrated formulation thus prepared can be used for the fluorescent whitening of paper or textile material, for example in detergents. To this end, they are in general diluted to the optimum concentration for the practical application by the addition of further auxiliaries or water.

The examples which follow illustrate the invention.

EXAMPLES

EXAMPLE 1

1:100 ml of a suspension containing 40% by weight of the active substance 4,4'-bis(2-sulfostyryl)biphenyl disodium salt, are heated in the form of any desired hydrate or any desired hydrate mixture to 95° C. in a sealed tube for 4 hours. This gives a past-like, brushable formulation.

Microscopic analysis shows that the only form left is the rod-like form. The X-ray diagram recorded using a Guinier camera in transmission geometry and Cu Kα1 radiation corresponds to that of the hydrate in the rod-like crystal form i as in Table 2.

To determine the water of hydration content, 200 mg of the hydrate mixture are equilibrated at a relative humidity of almost 100% and room temperature, heated to 200° C., and the weight loss is measured. It is convened into a hydrate of the formula (III).

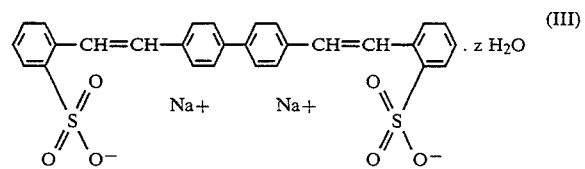

in which z is a number between 7 and 12.

EXAMPLE 2

To prepare platelet-like seed crystals, 500 g of the aqueous and salt-free suspension obtained as in Example 1 containing 40% by weight of the active substance 4,4-bis(2-sulfostyryl)biphenyl, disodium salt, in the rod-like form i are mixed with 500 ml of deionised water, and the mixture is stirred at 35° C. and 50 rpm for about 12 hours. The suspension thus obtained having an active substance content of 20% by weight is concentrated to about 45% by weight on a rotary evaporator at 25 mbar and 35° C.

Microscopic analysis shows that the only form left is the platelet-form p.

The X-ray diagram recorded using a Guinier camera in transmission geometry and Cu Kα1 radiation corresponds to that of Table 1.

The amount of bound water of hydration is determined by gravimetric analysis via the loss on drying at 200° C., the sample being first equilibrated at room temperature and a relative humidity of almost 100%. The unbound water present is determined by dynamic differential thermal analysis. To this end, 18 mg of the hydrate mixture cooled to −50° C., and the amount of absorbed heat is measured by heating at a heating rate of 10° C./min.

The measurements show that the hydrate has the formula (II)

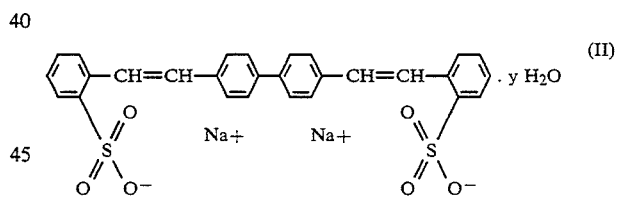

in which y is a number between 9 and 13.

EXAMPLE 3

500 g of the aqueous and salt-free suspension obtained as in Example 1 and containing 40% by weight of the active substance 4,4-bis(2-sulfostyryl)biphenyl, disodium salt, in the rod-like form i are mixed with 500 ml of deionised water, and the mixture is stirred at 35° C. and 50 rpm for about 12 hours. The suspension thus obtained having an active substance content of 20% by weight is cooled to 0°–5° C. and filtered through a vacuum nutsche filter. The resulting material on the nutsche filter has an active substance content of about 55% by weight and is diluted with deionised water to an active substance content of about 45% by weight.

Microscopic analysis shows that the only form left is the platelet-form p.

The X-ray diagram recorded using a Guinier camera in transmission geometry and Cu Kα1 radiation corresponds to that of Table 1.

EXAMPLE 4

2 tonnes of a 40% by weight suspension of the disodium salt of 4,4'-bis(2-sulfostyryl)biphenyl are added as platelet-like seed crystals to 8 tonnes of the 40% by weight suspension of the sodium salt of 4,4'-bis(2-sulfostyryl)biphenyl as produced, which is temperature-controlled at 15°–20° C. This mixture is slowly stirred at this temperature for 60 hours.

Microscopic analysis shows that the only form left is the platelet-form, the majority of the platelets being greater than 10 μm.

The X-ray diagram recorded using a Guinier camera in transmission geometry and Cu Kα1 radiation corresponds to that of Table 1.

Analysis of hydrate content is carded out as described in Example 2 and gives a compound of the formula (II)

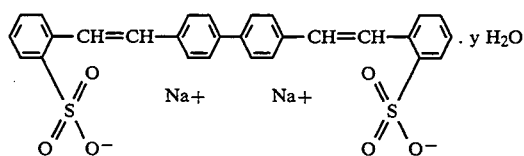

in which y is a number between 9 and 13.

EXAMPLE 5

1.5 tonnes of a 40% by weight suspension of the disodium salt of 4,4'-bis(2-sulfostyryl)biphenyl as produced is temperature-controlled at 15°–20° C., 1.5 tonnes of the suspension of platelet-like crystals obtained in Example 3 are added, and the mixture is slowly stirred at this temperature for 12 hours.

Microscopic analysis shows that the only form left is the platelet-like form, the majority of the platelets being greater than 10 μm.

The X-ray diagram recorded using a Guinier camera in transmission geometry and Cu Kα1 radiation corresponds to that of Table 1.

EXAMPLE 6

100 ml of the suspension obtained in Example 4 and containing 40% by weight of the active 4,4'-bis(2-sulfostyryl)biphenyl, disodium salt, in the platelet-like form are heated at 70° C. in a vessel equipped with reflux condenser for 4 hours. This gives a paste-like, brushable formulation.

Microscopic analysis shows that the only form left is the rod-like form.

The X-ray diagram recorded using a Guinier camera in transmission geometry and Cu Kα1 radiation corresponds to that of the hydrate in the rod-like crystal form j as in Table 3.

To determine the water of hydration content, 200 mg of the hydrate mixture are equilibrated at a relative humidity of almost 100% and room temperature, heated to 200° C., and the weight loss is measured. This gives a hydrate of the formula (III).

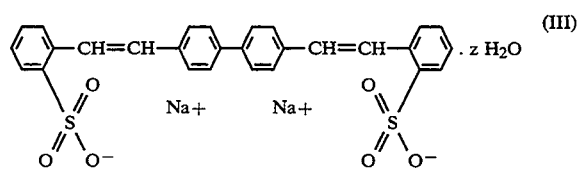

in which z is a number of between 7 and 12.

EXAMPLE 7

100 g each of the 40% by weight suspension of the rod-like forms i and j obtained in Example 1 and 6 are mixed with one another, giving a paste-like, brushable formulation.

The X-ray diagram recorded using a Guinier camera in transmission geometry and Cu Kα1 radiation corresponds to additive superposition of the lines according to Tables 2 and 3 as shown in Table 4.

EXAMPLE 8

9.9 tonnes of the 4% by weight suspensions of the hydrate in the platelet-like crystal form prepared as in Examples 3 and 4 are homogenised in a toothed colloid mill. 50 kg of 1,2-propylene glycol and 20 kg of Rhodopol 23 ® and 30 kg of Proxel GXL ® are added to the suspension, which is then homogenised again, giving 10 tonnes of an aqueous and flowable formulation of the disodium salt of 4,4'-bis(2-sulfostyryl)biphenyl containing about 40% by weight of active substance and being stable for months.

EXAMPLE 9

A) Preparation of seed crystals in the platelet-like (p) form:

500 g of a slurry containing 40% by weight of the active substance 4,4'-bis(2-sulfostyryl)biphenyl, sodium salt, am introduced into a reactor in the form of any desired hydrate or any desired hydrate mixture and stirred at 15 to 35° C. and 200 rpm.

500 g of deionised water are added, and the dry content is controlled (desired value=20% by weight of active substance). The 20% slurry is heated at 100° C. (reflux) for 15 to 30 minutes, during which the active substance goes in the solution. It is cooled to 35° C. over a period of 4 to 6 hours with stirring at 200 rpm. This results in recrystallisation of the active substance in the i form (rods).

The conversion process to give the p form is monitored by microscopic control, during which the temperature is maintained in the range 30 to 36° C. In the course of the process (about 4 to 10 hours), the viscosity of the slurry increases considerably. As soon as no more rods (i,j form) can be detected, the conversion process is complete, and the active substance is then present in the p form. The crystal size is less than 10 μm.

B) Conversion of the i crystal form into the p crystal form:

900 g of a slurry containing 40% by weight of the active substance 4,4'-bis(2-sulfostyryl)biphenyl, disodium salt, are introduced into a reactor in the form of any desired hydrate or any desired hydrate mixture and thoroughly stirred at 200 rpm and heated at 100° C. for at least 2 hours. The reactor contents are cooled to 35° C. over a period of 1 to 4 hours and temperature-controlled at this temperature. The active substance is now uniformly present in the i form.

180 g of a 20% slurry prepared as described in Example 9A) are admixed as seed crystals, and stirring of the slurry is continued at 200 rpm. A sample is taken from the reactor, and the dry content is determined (desired value=35.5 to 36% by weight). If necessary, the desired value is established by addition of water.

The conversion process is monitored by microscopic control. As soon as no more rods (i, j form) are detectable, the conversion process is complete.

The active substance is then present in the p form. The majority of the platelets is greater than 10 μm. The slurry is homogenised and, if inclusions of air are present, deaerated by applying vacuum.

EXAMPLE 10

100 g of the aqueous and salt-free suspension obtained as in Example 1 and containing 40% by weight of the active substance 4,4'-bis(2-sulfostyryl)biphenyl, disodium salt, in the rod-like form (i) are centrifuged at 10° C. and 10,000 rpm for 20 minutes. After the water has been decanted off, a paste-like bottom sediment remains which is spread over watch glass over a large area and equilibrated at a relative humidity of 70% and room temperature for 10 days.

The X-ray diagram recorded using a Guinier camera in transmission geometry and Cu Kα1 radiation corresponds to that of the hydrate in the crystal form (c) as in Table 5.

To determine the water of hydration, 200 mg of the hydrate are equilibrated at a relative humidity of almost 100% and room temperature and heated to 200° C. This gives a hydrate of the formula

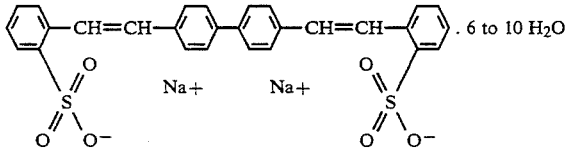

EXAMPLE 11:

100 g of the material obtained as in Example 7 and containing 40% by weight of the active substance 4,4'-bis(2-sulfostyryl)biphenyl, disodium salt, in the rod-like form (j) are centrifuged at 10° C. and 10,000 rpm for 20 minutes. After the water has been decanted off, a paste-like bottom sediment remain which is spread on a watch glass over a large area and equilibrated at a relative humidity of 75% and room temperature for 10 days. X-ray diagram and water content of the product obtained are identical to those of the product from Example 10.

EXAMPLE 12

3 liters of the suspension obtained in Example 4 and containing 40% by weight of the active substance 4,4'-bis(2-sulfostyryl)biphenyl, disodium salt, in the platelet-like form (p) are mixed in a flask equipped with reflux condenser with 150 g (5%) of NaCl with stirring at 50° C. for 2 days or at 100° C. for 2 hours. The X-ray diagram recorded using a Guinier camera in transmission geometry and Cu Kα1 radiation corresponds to that of the hydrate in the crystal form (c) as in Table 5.

TABLE 1

Hydrate of the disodium salt of 4,4'-bis(2-sulfostyryl)biphenyl in the platelet-like crystal form p

| d value [Å] | Intensity | d value [Å] | Intensity |
| --- | --- | --- | --- |
| 17.9 | weak | 3.77 | medium |
| 13.8 | very weak | 3.65 | very strong |
| 9.3 | medium | 3.58 | weak |
| 9.0 | very weak | 3.51 | strong |
| 7.7 | weak | 3.41 | very weak |
| 7.5 | very weak | 3.35 | weak |
| 7.3 | very weak | 3.21 | medium |
| 6.9 | very weak | 3.19 | strong |
| 6.3 | weak | 3.14 | weak |
| 6.1 | strong | 3.07 | weak |
| 5.75 | very strong | 3.05 | weak |
| 5.60 | weak | 3.03 | weak |
| 5.35 | strong | 3.02 | very weak |
| 5.19 | very weak | 2.98 | weak |
| 5.04 | strong | 2.96 | very weak |
| 4.81 | strong | 2.90 | medium |
| 4.67 | weak | 2.88 | weak |
| 4.55 | weak | 2.85 | very weak |
| 4.50 | very weak | 2.78 | very weak |
| 4.35 | medium | 2.68 | weak |
| 4.12 | weak | 2.65 | medium |
| 4.00 | very weak | 2.62 | weak |
| 3.90 | strong | 2.56 | very weak |
| 3.85 | strong | | |

TABLE 2

Hydrate of the disodium salt of 4,4'-bis(2-sulfostyryl)biphenyl in the rod-like crystal form i.

| d value [Å] | Intensity | d value [Å] | Intensity |
| --- | --- | --- | --- |
| 18.6 | very weak | 4.49 | very weak |
| 12.1 | weak | 4.43 | weak |
| 9.3 | very weak | 4.37 | very weak |
| 9.0 | very weak | 4.25 | weak |
| 8.8 | very weak | 4.17 | weak |
| 7.2 | weak | 4.00 | very weak |
| 6.8 | weak | 3.95 | medium |
| 6.7 | very strong | 3.93 | weak |
| 6.4 | medium | 3.86 | medium |
| 5.97 | medium | 3.73 | weak |
| 5.78 | very weak | 3.68 | weak |
| 5.71 | weak | 3.63 | weak |
| 5.35 | weak | 3.59 | weak |
| 5.07 | medium | 3.38 | very weak |
| 4.90 | very weak | 3.32 | weak |
| 4.84 | very strong | 3.30 | weak |
| 4.79 | strong | 3.19 | very weak |
| 4.53 | very weak | 3.00 | very weak |

TABLE 3

Hydrate of the disodium salt of 4,4'-bis(2-sulfostyryl)biphenyl in the rod-like crystal form j.

| d value [Å] | Intensity | d value [Å] | Intensity |
| --- | --- | --- | --- |
| 19.8 | very weak | 4.73 | very strong |
| 11.1 | medium | 4.62 | weak |
| 7.0 | weak | 4.60 | strong |
| 6.9 | very strong | 4.40 | weak |
| 6.4 | strong | 4.36 | very weak |
| 6.3 | weak | 4.25 | very weak |
| 6.0 | very weak | 4.20 | strong |
| 5.88 | weak | 4.11 | strong |
| 5.71 | weak | 3.88 | weak |
| 5.63 | medium | 3.86 | medium |
| 5.55 | weak | 3.75 | medium |
| 5.29 | weak | 3.69 | medium |
| 5.17 | very weak | 3.32 | very weak |
| 5.13 | weak | 3.25 | weak |
| 5.01 | strong | 3.11 | weak |
| 4.95 | medium | 3.05 | weak |
| 4.86 | very weak | | |

TABLE 4

Mixture of the hydrates of the rod-like crystal forms i and j of the disodium salt of 4,4'-bis(2-sulfostyryl)biphenyl.

| d value [Å] | Intensity | d value [Å] | Intensity |
|---|---|---|---|
| 19.7 | weak | 4.60 | strong |
| 18.7 | weak | 4.48 | very weak |
| 11.1 | medium | 4.40 | weak |
| 7.0 | weak | 4.37 | very weak |
| 6.9 | strong | 4.26 | weak |
| 6.6 | very strong | 4.21 | strong |
| 6.4 | very strong | 4.12 | strong |
| 6.3 | weak | 3.87 | strong |
| 5.93 | (broad) medium | 3.75 | medium |
| 5.71 | medium | 3.69 | medium |
| 5.64 | medium | 3.63 | very weak |
| 5.56 | weak | 3.59 | very weak |
| 5.30 | medium | 3.37 | very weak |
| 5.13 | weak | 3.32 | weak |
| 5.06 | medium | 3.30 | weak |
| 5.01 | very strong | 3.25 | weak |
| 4.96 | medium | 3.18 | very weak |
| 4.84 | (broad) strong | 3.12 | very weak |
| 4.79 | strong | 3.06 | very weak |
| 4.73 | strong | | |

TABLE 5

Hydrate of the disodium salt of 4,4'-bis(2-sulfostyryl)biphenyl in the crystal form c

| d value [Å] | Intensity | d value [Å] | Intensity |
|---|---|---|---|
| 16.7 | weak | 4.12 | very strong |
| 14.4 | strong | 4.01 | weak |
| 12.0 | very weak | 3.98 | very weak |
| 10.8 | medium | 3.85 | medium |
| 8.3 | weak | 3.72 | weak |
| 7.2 | medium | 3.64 | medium |
| 6.6 | weak | 3.56 | very weak |
| 6.4 | weak | 3.52 | very weak |
| 6.1 | weak | 3.49 | very weak |
| 5.98 | very weak | 3.36 | weak |
| 5.51 | medium | 3.31 | weak |
| 5.42 | very strong | 3.29 | weak |
| 5.25 | weak | 3.21 | very weak |
| 5.18 | weak | 3.14 | weak |
| 4.90 | weak | 3.06 | very weak |
| 4.85 | weak | 2.98 | very weak |
| 4.75 | medium | 2.93 | weak |
| 4.71 | weak | 2.86 | weak |
| 4.65 | weak | 2.81 | very weak |
| 4.58 | strong | 2.76 | very weak |
| 4.32 | medium | 2.71 | very weak |

TABLE 6

Hydrate of the dipotassium salt of 4,4'-bis(2-sulfostyryl)biphenyl

| d value [Å] | Intensity | d value [Å] | Intensity |
|---|---|---|---|
| 15.9 | very strong | 4.91 | weak |
| 15.1 | strong | 4.80 | very weak |
| 12.8 | very weak | 4.72 | weak |
| 11.5 | weak | 4.67 | very weak |
| 10.5 | strong | 4.48 | very weak |
| 7.5 | very weak | 4.41 | strong |
| 6.4 | medium | 4.39 | medium |
| 6.1 | strong | 4.25 | very weak |
| 5.82 | very weak | 4.22 | very weak |
| 5.75 | very weak | 4.11 | very weak |
| 5.67 | weak | 4.05 | very weak |
| 5.61 | weak | 3.97 | weak |
| 5.54 | weak | 3.81 | medium |
| 5.47 | medium | 3.77 | weak |
| 5.43 | very weak | 3.72 | weak |
| 5.29 | very weak | 3.69 | weak |
| 5.01 | very strong | | |

We claim:

1. A hydrate of the disodium salt or dipotassium salt of 4,4'-bis(2-sulfostyryl)biphenyl whose crystal form is characterised by an X-ray diffraction diagram which is essentially as in Table 1, 2, 3, 5 or 6 or a mixture of hydrates of the disodium salt of 4,4'-bis(2-sulfostyryl)-biphenyl whose crystal forms are essentially characterised by additive superpositions of the lines according to Tables 2 and 3, as shown in Table 4.

2. A hydrate in the rod-like crystal form of the disodium salt of 4,4'-bis(2-sulfostyryl)biphenyl according to claim 1 characterised by an X-ray diffraction diagram which is essentially as in Table 2 or 3 or a mixture of the two rod-like crystal forms corresponding to additive superposition of the lines according to Tables 2 and 3, as shown in Table 4.

3. A hydrate of the rod-like crystal form of the disodium salt of 4,4'-bis(2-sulfostyryl)biphenyl according to claim 2 of the formula (III)

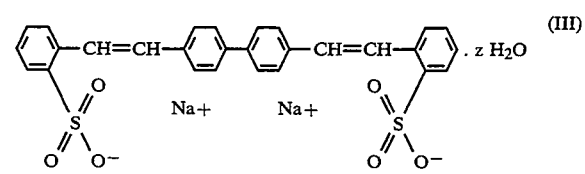

in which z is a number of between 7 and 12.

4. A hydrate in the crystal form c of the disodium salt of 4,4'-bis(2-sulfostyryl)biphenyl according to claim 1 characterised by an X-ray diffraction diagram which is essentially as in Table 5.

5. A hydrate of the platelet-like crystal form of the disodium salt of 4,4'-bis(2-sulfostyryl)biphenyl according to claim 4 of the formula (IV)

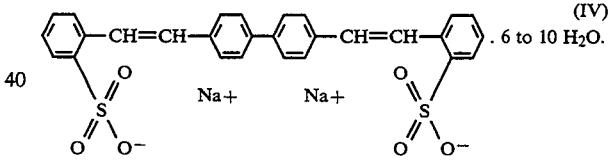

6. A hydrate of the dipotassium salt of 4,4'-bis(2-sulfostyryl)biphenyl according to claim 1 characterised by an X-ray diffraction diagram which is essentially as in Table 6.

7. A hydrate of the disodium salt of 4,4'-bis(2-sulfostyryl)biphenyl according to claim 6 of the formula (V)

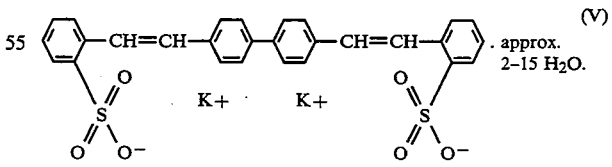

8. A hydrate in the platelet-like crystal form of the disodium salt of 4,4'-bis(2-sulfostyryl)biphenyl according to claim 1 characterised by an X-ray diffraction diagram which is essentially as in Table 1.

9. A hydrate of the platelet-like crystal form (p) of the disodium salt of 4,4'-bis(2-sulfostyryl)biphenyl according to claim 8 of the formula (II)

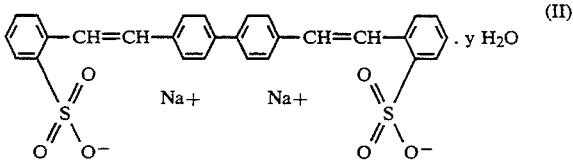

(II)

in which y is a number between 9 and 13.

10. A process for the preparation of the platelet-like (p) crystal form according to claim 8, which comprises stirring an aqueous suspension of the disodium salt of 4,4'-bis(2-sulfostyryl)biphenyl having a maximum active substance content of 20% by weight in the form of hydrate having an X-ray diffraction diagram which is essentially as in Table 2, 3 or 4, at 5 to 45° C. and a low shearing force for more than 4 hours.

11. A process for the preparation of the platelet-like (p) crystal form according to claim 8, which comprises adding seed crystals to an aqueous suspension of any desired hdyrate.

12. A process for the preparation of the platelet-like (p) crystal form according to claim 11, wherein an aqueous suspension having an active substance content of 30–50% by weight is used.

13. A process for the preparation of the platelet-like (p) crystal form according to claim 11 wherein
 a) the disodium salt of 4,4'-bis(2-sulfostyryl)biphenyl as prepared is homogenised,
 b) seed crystals are added and
 c) the mixture is stirred.

14. A process for the preparation of the platelet-like (p) crystal form according to claim 13, wherein stirring is carded out intermittently.

15. A process for the preparation of the platelet-like (p) crystal form according to claim 11 wherein the process is carded out at a temperature of 5°–45° C.

16. A process for the preparation of the platelet-like (p) crystal form according to claim 15, wherein the process is carried out at a temperature of 15°–40° C.

17. A process for the preparation of the platelet-like (p) crystal form according to claim 11 wherein the seed crystal content is between 0.1 and 60% by weight, relative to the overall content of the disodium salt of 4,4'-bis(2-sulfostyryl)biphenyl.

18. A process for the preparation of the compound of the platelet-like (p) crystal form according to claim 17, wherein the seed crystal content is between 1 and 50% by weight, relative to the overall content of the disodium salt of 4,4'-bis(2-sulfostyryl)biphenyl.

19. A process for the preparation of the compound of the platelet-like (p) crystal form according to claim 18, wherein the seed crystal content is between 1 and 30% by weight, relative to the overall content of the disodium salt of 4,4'-bis(2-sulfostyryl)biphenyl.

20. A process according to claim 11 for the preparation of the platelet-like (p) crystal form of the disodium salt of 4,4'-bis(2-sulfostyryl)biphenyl characterized by an X-ray diffraction diagram which is essentially as in Table 1, wherein an aqueous suspension of a rod-like form characterized by an X-ray diffraction diagram which is essentially as in Table 2 or 3 or a mixture of the two rod-like crystal forms corresponding to additive superposition of the lines according to Tables 2 and 3 as shown in Table 4, is inoculated with 0.1 to 5% by weight of seed crystals of said platelet-like (p) crystal form, relative to the overall active substance content.

21. A process for the preparation of the platelet-like (p) crystal form according to claim 20, wherein the seed crystals have an average size not exceeding 10 μm.

22. A process for the preparation of the platelet-like (p) crystal form according to claim 20, wherein conversion is effected without stirring.

23. A flowable aqueous formulation containing 30–50% by weight of the active substance 4,4'-bis(2-sulfostyryl)biphenyl, sodium salt, wherein the 4,4'-bis(2-sulfostyryl)biphenyl, disodium salt, is present in the platelet-like crystal form according to claim 8.

24. A flowable aqueous formulation according to claim 23, wherein the particle size of the majority of the platelet-like crystals is above 10 μm.

25. A formulation according to claim 23, which contains additional formulation auxiliaries, selected from dispersants, builders, protective colloids, stabilisers, preservatives, perfuming agents and sequestering agents.

26. A formulation according to claim 25, which additionally contains
 a) 0.3–1% by weight of propylene glycol,
 b) 0. 1–0.5% by weight of a heteropolysaccharide of the xanthan type,
 c) 0.1–0.5% by weight of 1,2-benzisothiazolin-3-one and
 d) water.

27. A formulation according to claim 25, which contains 0.2 to 5% by weight of propylene glycol.

28. A formulation according to claim 25, which contains 0.1 to 1% by weight of 1,2-benzisothiazolin-3-one.

29. A formulation according to claim 25, which contains 0.01 to 2% by weight of a heteropolysaccharide of the xanthan type.

30. A process for the preparation of the platelet-like (p) crystal form according to claim 8, which comprises mixing dried starting material with seed crystals and leaving the mixture at a relative humidity of 90–100% and 20°–55° C. in a thin layer for several days.

31. A process for the preparation of the rod-like crystal form according to claim 2 and Table 2, which comprises heating an aqueous suspension of any desired hydrate of the disodium salt of 4,4'-bis(2-sulfostyryl)biphenyl at a temperature of 70°–130° C. for 2–12 hours and then cooling it to room temperature.

32. A process for the preparation of the rod-like crystal form according to claim 31, which comprises treating an aqueous suspension containing 40 wt. % of any desired hydrate of the disodium salt of 4,4'-bis(2-sulfostyryl)biphenyl for 4 hours at a temperature of 95° C. in a closed vessel, and then cooling to room temperature.

33. A viscous aqueous formulation containing 30–50% by weight of the active substance 4,4'-bis(2-sulfostyryl)biphenyl, disodium salt, wherein the 4,4'-bis(2-sulfostyryl)biphenyl, disodium salt, is present in the rod-like crystal form according to claim 2.

34. A process for the preparation of the rod-like crystal form according to claim 2 and Table 3, which comprises heating the aqueous suspension of any desired hydrate of the disodium salt of 4,4'-bis(2-sulfostyryl)biphenyl at a temperature of 50°–70° C. for 2 hours to 4 days and then cooling it to room temperature.

35. A process for the preparation of the rod-like crystal form according to claim 2 and Table 3, which comprises treating an aqueous suspension containing 40 wt. % of disodium salt of 4,4'-bis(2-sulfostyryl)biphenyl in the platelet form for 4 hours at a temperature of 95° C.

in a closed vessel, and then cooling to room temperature.

36. A process for the preparation of the hydrates in the crystal form (c) of the disodium salt of 4,4'-bis(2-sulfostyryl)biphenyl according to claim 4 and Table 5, which comprises stirring at least about 5 wt. % NaCl, based on the total weight of the suspension, with a suspension of the hydrates (i), (j) or (p) at room temperature or up to 100° C., and then cooling.

37. A process for the preparation of the platelet-like (p) crystal form according to claim 11, wherein
 a) the disodium salt of 4,4'-bis(2-sulfostyryl)biphenyl as prepared is suspended to give a suspension having an active substance content of 30–50% by weight, and the suspension is homogenised,
 b) 1–50% by weight of platelet-like seed crystals, relative to the overall content of the disodium salt of 4,4'-bis(2-sulfostyryl)biphenyl, are added,
 c) the suspension is stirred at 15°–40° C. for 2–16 hours,
 d) homogenised again and
 e) deaerated by applying vacuum.

38. A process for the preparation of the hydrates in the platelet-like crystal form (c) of the disodium salt of 4,4'-bis(2-sulfostyryl)biphenyl according to claim 4 and Table 5, which comprises removing a portion of the water of an aqueous suspension of the hydrates in the (i) or (j) rod-like form or in the p platelet-form and then stirring the suspension, depending on the established relative humidity of 52% up to 100%, for a period ranging from hours to days.

* * * * *